United States Patent
Kondo et al.

(10) Patent No.: US 12,380,970 B2
(45) Date of Patent: Aug. 5, 2025

(54) IMAGE PROCESSING APPARATUS AND METHOD FOR CONTROLLING THE SAME

(71) Applicant: CANON KABUSHIKI KAISHA, Tokyo (JP)

(72) Inventors: Yuichi Kondo, Chiba (JP); Satohiro Oga, Chiba (JP)

(73) Assignee: Canon Kabushiki Kaisha, Tokyo (JP)

( * ) Notice: Subject to any disclaimer, the term of this patent is extended or adjusted under 35 U.S.C. 154(b) by 536 days.

(21) Appl. No.: 17/720,965

(22) Filed: Apr. 14, 2022

(65) Prior Publication Data

US 2022/0336065 A1 Oct. 20, 2022

(30) Foreign Application Priority Data

Apr. 16, 2021 (JP) .................................. 2021-069802

(51) Int. Cl.
  *G16H 10/60* (2018.01)
  *H04N 1/00* (2006.01)

(52) U.S. Cl.
  CPC ......... *G16H 10/60* (2018.01); *H04N 1/00209* (2013.01); *H04N 1/00236* (2013.01); *H04N 1/00244* (2013.01)

(58) Field of Classification Search
  CPC ........ G16H 10/60; G16H 30/40; G16H 40/20; H04N 1/00209; H04N 1/00236; H04N 1/00244
  USPC ......................................................... 705/2, 3
  See application file for complete search history.

(56) References Cited

U.S. PATENT DOCUMENTS

| | | | |
|---|---|---|---|
| 8,090,742 B2* | 1/2012 | Mok | G16H 30/20 705/2 |
| 2008/0117472 A1* | 5/2008 | Nohtomi | H04N 1/2175 358/403 |
| 2016/0274745 A1* | 9/2016 | Baba | G06F 3/0482 |
| 2017/0270248 A1* | 9/2017 | Kishimoto | G16H 10/60 |
| 2020/0293489 A1* | 9/2020 | Bell | G06F 16/14 |

FOREIGN PATENT DOCUMENTS

| | | | |
|---|---|---|---|
| JP | 2007013887 A | | 1/2007 |
| JP | 2008129951 A | | 6/2008 |
| JP | 2014120083 A | * | 6/2014 |

OTHER PUBLICATIONS

Pacific Clinics, "DMH EHRS Forms and Attachments Naming Conventions," https://pcweb.pacificclinics.org/wp-content/uploads/2021/05/DMH-FormsAttachments NamingConventions20200901.pdf Aug. 31, 2020.*

* cited by examiner

*Primary Examiner* — Joshua B Blanchette

(74) *Attorney, Agent, or Firm* — Canon U.S.A., Inc. IP Division

(57) ABSTRACT

An image processing apparatus includes a generation unit configured to read an image of a document and to generate an image file based on the read image, a transmission unit configured to transmit the image file generated by the generation unit, a determination unit configured to determine a file name of the image file, and a reception unit configured to receive patient information from an information processing apparatus. The determination unit determines the file name of the image file based on patient information selected by a user from the patient information received by the reception unit.

7 Claims, 20 Drawing Sheets

FIG.5

■ PATIENT INFORMATION DB ~501

| PATIENT NUMBER | PATIENT NAME | TREATMENT STATUS | CLINICAL DEPARTMENT | ADDRESS | POINT OF CONTACT | ... |
|---|---|---|---|---|---|---|
| 1122 | AAAAA | OUTPATIENT (NEW) | INTERNAL MEDICINE DEPARTMENT | | | |
| 2233 | BBBBB | OUTPATIENT (NEW) | DERMATOLOGY DEPARTMENT | | | |
| 3344 | CCCCC | OUTPATIENT (CURRENT DAY) | SURGICAL DEPARTMENT | | | |
| 4455 | DDDDD | OUTPATIENT (CURRENT DAY) | PEDIATRIC DEPARTMENT | | | |
| 5566 | EEEEE | PAID | DERMATOLOGY DEPARTMENT | | | |
| 6677 | FFFFF | HOSPITALIZATION | OBSTETRICS AND GYNECOLOGY DEPARTMENT | | | |

■ CLASSIFICATION INFORMATION ~502

| DOCUMENT CLASSIFICATION |
|---|
| MEDICAL QUESTIONNAIRE |
| REFERRAL FORM |
| HEALTH INSURANCE CARD |
| MEDICATION RECORD |
| MEDICAL CERTIFICATE |

FIG.6A

| 601 | | | 602 | | | |
|---|---|---|---|---|---|---|
| PATIENT SELECTION | ALL | OUTPATIENT (NEW) | OUTPATIENT (CURRENT DAY) | HOSPITALIZATION | ◀ | ▶ |
| 604 — 1122 AAAAA —605 | | | OUTPATIENT (NEW) —606 | | △ | —607 |
| 2233 BBBBB | | | OUTPATIENT (NEW) | | ≡ | |
| 603 — 3344 CCCCC | | | OUTPATIENT (CURRENT DAY) | | | |
| 4455 DDDDD | | | OUTPATIENT (CURRENT DAY) | | | |
| 5566 EEEEE | | | PAID | | ▽ | |

FIG.6B

| PATIENT SELECTION | ALL | OUTPATIENT (NEW) | OUTPATIENT (CURRENT DAY) | HOSPITALIZATION | ◀ | ▶ |
|---|---|---|---|---|---|---|
| 1122 AAAAA | | | OUTPATIENT (NEW) | | △ | |
| 2233 BBBBB | | | OUTPATIENT (NEW) | | ≡ | |
| | | | | | | |
| | | | | | | |
| | | | | | ▽ | |

FIG.6C

| PATIENT SELECTION | ALL | OUTPATIENT (NEW) | OUTPATIENT (CURRENT DAY) | HOSPITALIZATION | ◀ | ▶ |
|---|---|---|---|---|---|---|
| 3344 CCCCC | | | OUTPATIENT (CURRENT DAY) | | | |
| 4455 DDDDD | | | OUTPATIENT (CURRENT DAY) | | | |
| | | | | | | |
| | | | | | | |
| | | | | | | |

FIG.6D

| PATIENT SELECTION | OUTPATIENT (CURRENT DAY) | HOSPITALIZATION | PAID | | ◀ | ▶ |
|---|---|---|---|---|---|---|
| 5566 EEEEE | | | PAID | | | |
| | | | | | | |
| | | | | | | |
| | | | | | | |
| | | | | | | |

FIG.14A

| PATIENT SELECTION | OUTPATIENT (NEW) |
|---|---|
| 1122 | AAAAA |
| 2233 | BBBBB |
| | |
| | |
| | |
| | |

FIG.14B

| PATIENT SELECTION | OUTPATIENT (CURRENT DAY) |
|---|---|
| 3344 | CCCCC |
| 4455 | DDDDD |
| | |
| | |
| | |
| | |

FIG.16

CLASSIFICATION SELECTION ~1601

- MEDICAL QUESTIONNAIRE
- REFERRAL FORM
- HEALTH INSURANCE CARD — 1603
- MEDICATION RECORD
- [REGISTERED] MEDICAL CERTIFICATE — 1604

1610

THE ITEM ALREADY REGISTERED IS SELECTED.
DO YOU WANT TO RE-REGISTER IT?

YES (1611)   NO (1612)

HOME

1620

RE-REGISTRATION IS PROHIBITED.

OK (1621)

HOME

FIG.17

| 1701 | 1702 | 1703 | 1704 | 1705 |
|---|---|---|---|---|
| PATIENT NUMBER | DOCUMENT CLASSIFICATION | PREVIOUSLY REGISTERED TIME | PERMISSION OR NON-PERMISSION OF RE-REGISTRATION | RE-REGISTRATION AVAILABLE TIME |
| 1111 | HEALTH INSURANCE CARD | 20201003 0916 | PERMITTED | 2592000 |
| 1111 | MEDICAL QUESTIONNAIRE | 20100630 0815 | NOT PERMITTED | — 1712 |
| 1111 | MEDICATION RECORD | 00000000 0000 | PERMITTED | 2592000 |
| ... | ... | ... | ... | ... |
| ... | ... | ... | ... | ... |

1700, 1711

IMAGE PROCESSING APPARATUS AND METHOD FOR CONTROLLING THE SAME

BACKGROUND

Field of the Disclosure

The present disclosure relates to an image processing apparatus and a method for controlling the same.

Description of the Related Art

Japanese Patent Application Laid-Open No. 2007-13887 discusses a technique in which a read document is divided into a plurality of files, and a file name set in advance is assigned to each file.

For example, in a medical institution, a plurality of document types, such as a referral form from another hospital, a health insurance card, and a medical questionnaire, is supplied from a patient who comes to the medical institution. In order to automatically register these documents in an electronic medical chart system, it is necessary to add identification information associated with the patient and classification information of the document to an image file of each read document. As a method for adding identification information and classification information to an image file, there is a method for adding the above-described information to a file name.

As a method for assigning a file name to an image file as described above, there is a method for selecting information to be assigned to a file name from a list in addition to a method for setting a file name by inputting it from an operation unit. Such a method can save a user the trouble of inputting the file name each time.

However, in a case where an image file is stored in an electronic medical chart system using an image forming apparatus, it is necessary to register a lot of patient information and classification information of documents in advance as a list of information to be assigned to a file name. It is also necessary to reset patient identification information that changes from day to day, and it is thus time-consuming.

SUMMARY

Some embodiments of the present disclosure are made in view of the above-described issues and are directed to a technique for easily registering information used in a file name of an image file to be stored in an electronic medical chart system.

According to an aspect of the present disclosure, an image processing apparatus includes a generation unit configured to read an image of a document and to generate an image file based on the read image, a transmission unit configured to transmit the image file generated by the generation unit, a determination unit configured to determine a file name of the image file, and a reception unit configured to receive patient information from an information processing apparatus. The determination unit determines the file name of the image file based on patient information selected by a user from the patient information received by the reception unit.

Further features of various embodiments will become apparent from the following description of exemplary embodiments with reference to the attached drawings.

BRIEF DESCRIPTION OF THE DRAWINGS

FIG. 5 illustrates an example of a patient information database (DB) and classification information in the electronic medical chart system server.

FIGS. 6A to 6D illustrate examples of an execution screen of an electronic medical chart cooperation application that is executed in a case where an electronic medical chart cooperation button is pressed.

FIGS. 14A and 14B illustrate examples of a patient selection screen of the electronic medical chart cooperation application.

FIG. 16 illustrates examples of a document classification selection screen at a time of preventing double registration.

FIG. 17 illustrates an example of document classification information to be acquired by communicating with the electronic medical chart system server.

DESCRIPTION OF THE EMBODIMENTS

Exemplary embodiments of the present disclosure will be described in detail below with reference to the attached drawings. Configurations according to the exemplary embodiments described below are merely examples, and some embodiments are not limited to the described configurations.

Figure 1:
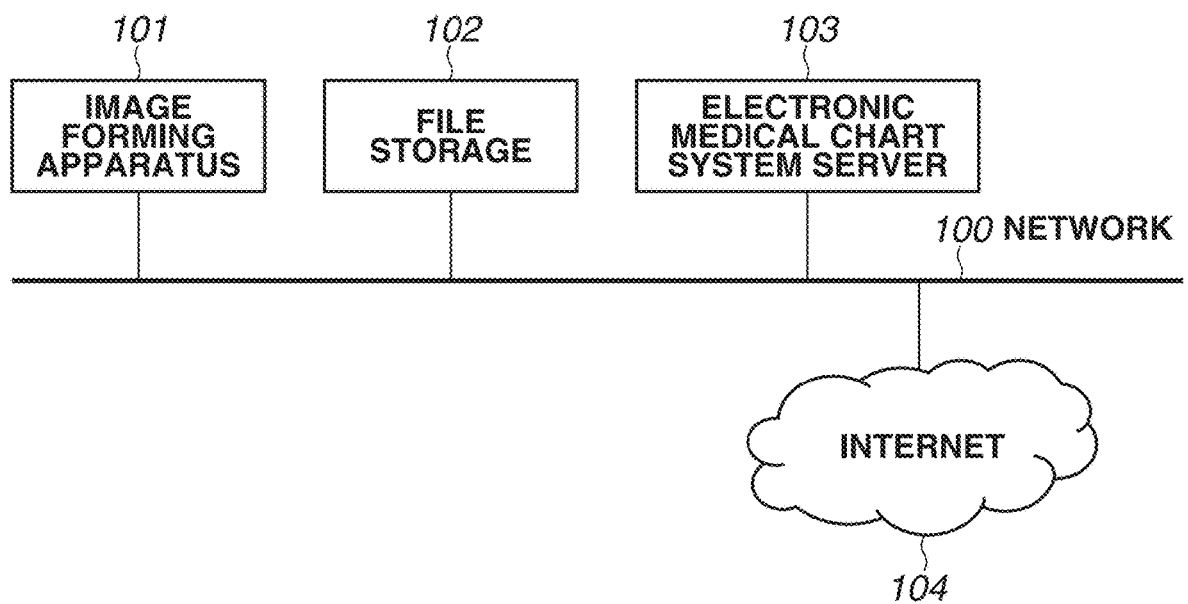
FIG. 1 is a block diagram illustrating an example of a network configuration.

FIG. 1 illustrates an example of a network configuration. According to a first exemplary embodiment, an image forming apparatus 101, a file storage 102, and an electronic medical chart system server 103 are connected to a network 100 and are in a communicable state with each other. The network 100 is connected to the Internet 104.

The image forming apparatus 101 also serving as an image processing apparatus transmits image data acquired by reading a document to the file storage 102 a file server to store the image data therein. The electronic medical chart system server 103 serving as an information processing apparatus refers to the image data in the file storage 102 and registers the image data in the electronic medical chart system. The file storage 102 and the electronic medical chart system server 103 may exist in the same apparatus. The file storage 102 and the electronic medical chart system server 103 may be in the communicable state with the image forming apparatus 101 via the Internet 104, not via the network 100.

Examples of the image data described in the present exemplary embodiment include document data in a Portable Document Format (PDF) format, and image data in an image format, such as a Tagged Image File Format (TIFF) and a Joint Photographic Experts Group (JPEG) format.

Figure 2:
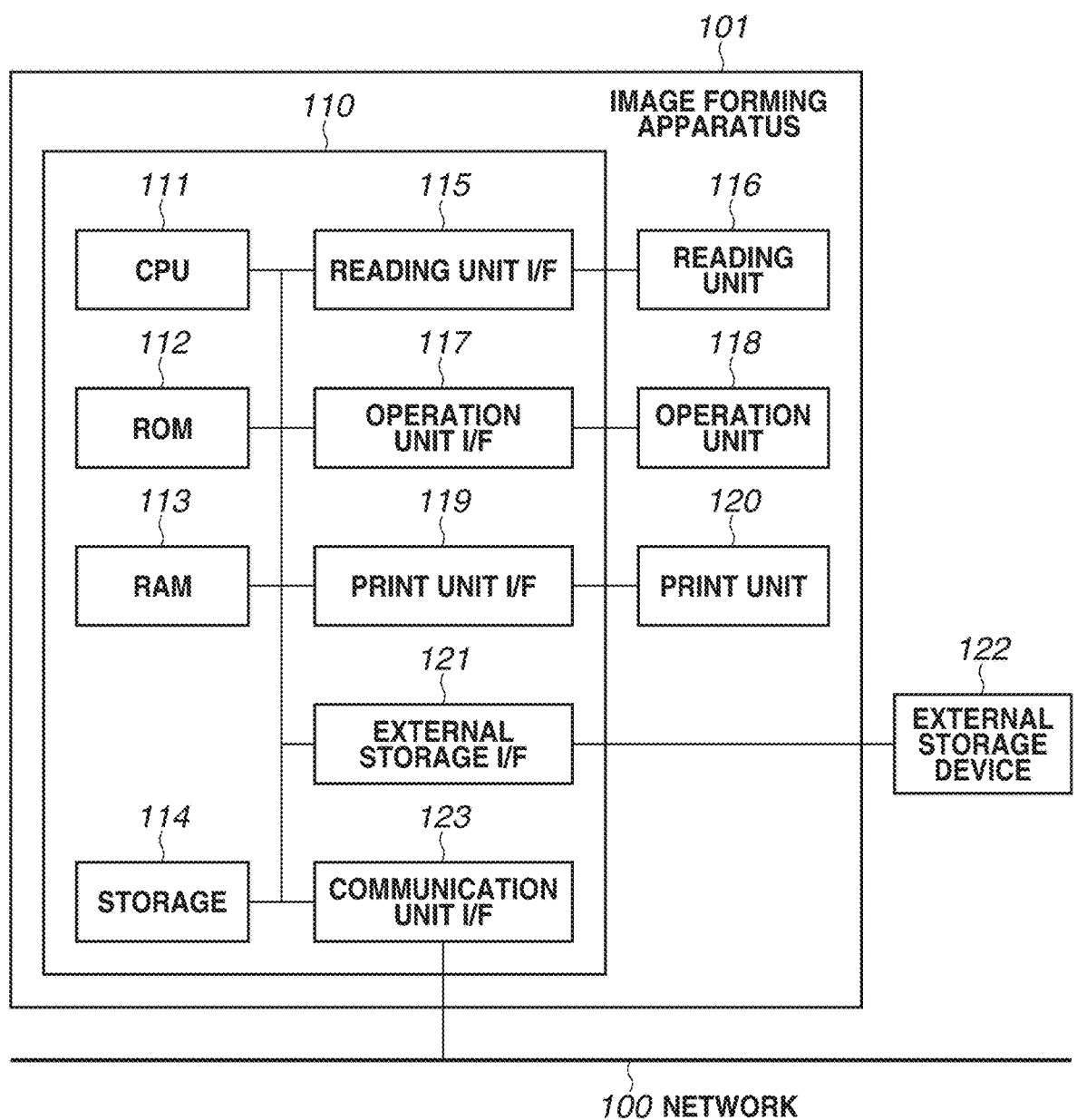
FIG. 2 is a block diagram illustrating an example of a hardware configuration of an image forming apparatus.

FIG. 2 illustrates an example of a hardware configuration of the image forming apparatus 101. A control unit 110 including a central processing unit (CPU) 111 controls operations of the entire image forming apparatus 101. The CPU 111 reads a control program stored in a read-only memory (ROM) 112 or a storage 114 and performs various types of control, such as read control and print control. The ROM 112 stores a control program that can be executed by the CPU 111. The ROM 112 also stores, for example, a boot program and font data. A random access memory (RAM) 113 is a main storage memory of the CPU 111 and is used as a temporary storage area for developing various control programs stored in a work area, the ROM 112, and the storage 114. The storage 114 stores image data, print data, an address book, various programs, and various types of setting information therein. According to the present exemplary embodiment, a flash memory is assumed as the storage 114, but an auxiliary storage device, such as a solid state drive (SSD), a hard disk drive (HDD), and an embedded MultiMediaCard (eMMC), may be used.

The image forming apparatus 101 causes one CPU 111 to execute each processing illustrated in flowcharts described below using one memory (the RAM 113), but another configuration may be used. For example, each processing illustrated in the flowcharts described below can be executed by a plurality of CPUs, RAMs, ROMs, and storages in cooperation with each other. Alternatively, a hardware circuit, such as an application specific integrated circuit (ASIC) and a field-programmable gate array (FPGA), may be used to execute a part of the processing.

A reading unit interface (I/F) 115 connects a reading unit 116 to the control unit 110. The reading unit 116 reads an image on a document and converts the read image into image data, such as binary data. The image data generated by the reading unit 116 is transmitted to an external apparatus, stored in an external storage apparatus, or printed on a recording sheet.

An operation unit IN 117 connects an operation unit 118 to the control unit 110. The operation unit 118 displays information to a user and detects an input from the user.

A print unit IN 119 connects a print unit 120 to the control unit 110. The CPU 111 transfers image data to be printed (image data as a print target) to the print unit 120 via the print unit IN 119. The print unit 120 prints an image on a recording sheet fed from a sheet feeding cassette (not illustrated).

An external storage IN 121 connects an external storage device 122 to the control unit 110. The CPU 111 stores the image data in the external storage device 122 via the external storage I/F 121. According to the present exemplary embodiment, a universal serial bus (USB) interface and a USB memory are respectively assumed as the external storage IN 121 and the external storage device 122, but an external storage device, such as a secure digital (SD) card, may be used.

The control unit 110 is connected to the network 100 by a communication unit OF 123. The communication unit IN 123 transmits the image data to and receives print data from the external apparatus via the network 100.

Figure 3:
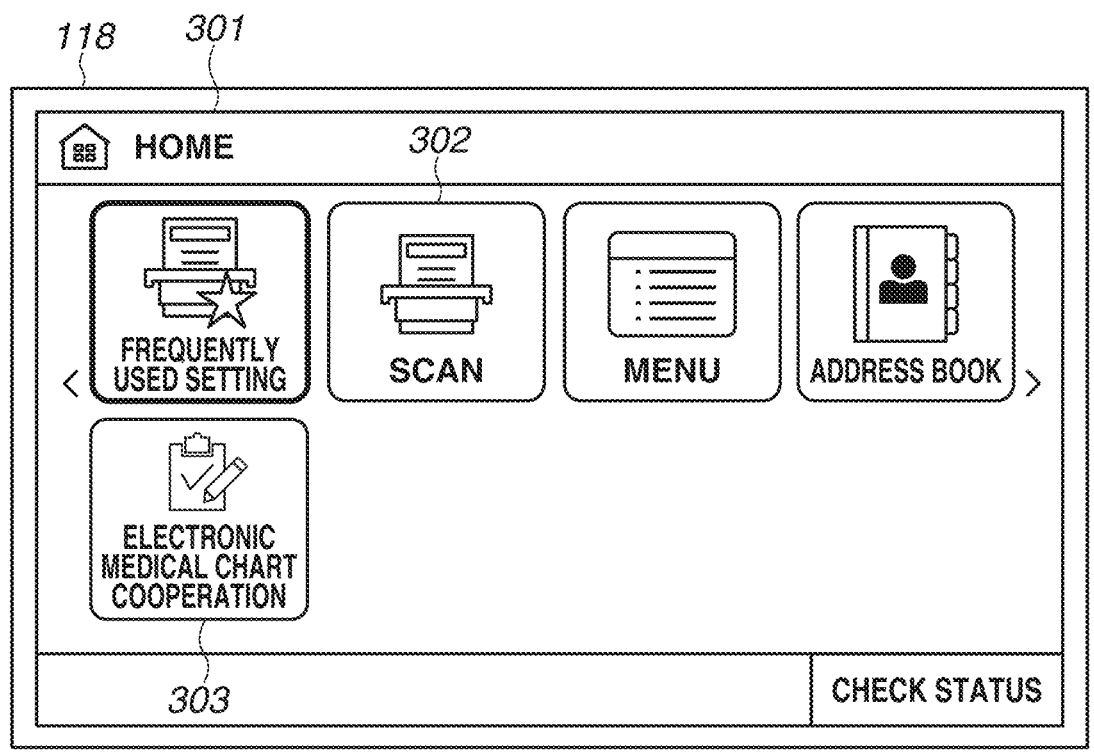
FIG. 3 illustrates an example of a home screen displayed immediately after start-up of the image forming apparatus.

FIG. 3 illustrates an example of a home screen displayed immediately after start-up of the image forming apparatus 101. The home screen is a screen for instructing execution of each function of the image forming apparatus 101 and is displayed on a touch panel screen included in the operation unit 118. In the home screen, icon images of respective functions, such as "frequently used setting", "scan", "menu", and "address book", executed by the image forming apparatus 101 are displayed.

A screen area 301 is an area in which a name of a current screen is displayed, and a name "home" is displayed. A function button 302 is a button for executing each function provided in the image forming apparatus 101, and a corresponding function is executed if the button is pressed. One of function button pages in which a plurality of the function buttons 302 is arranged is displayed on the screen. An electronic medical chart cooperation button 303 is a button for scanning, for example, a referral form, and a medical questionnaire and storing generated image data in the file storage 102.

Figure 4:
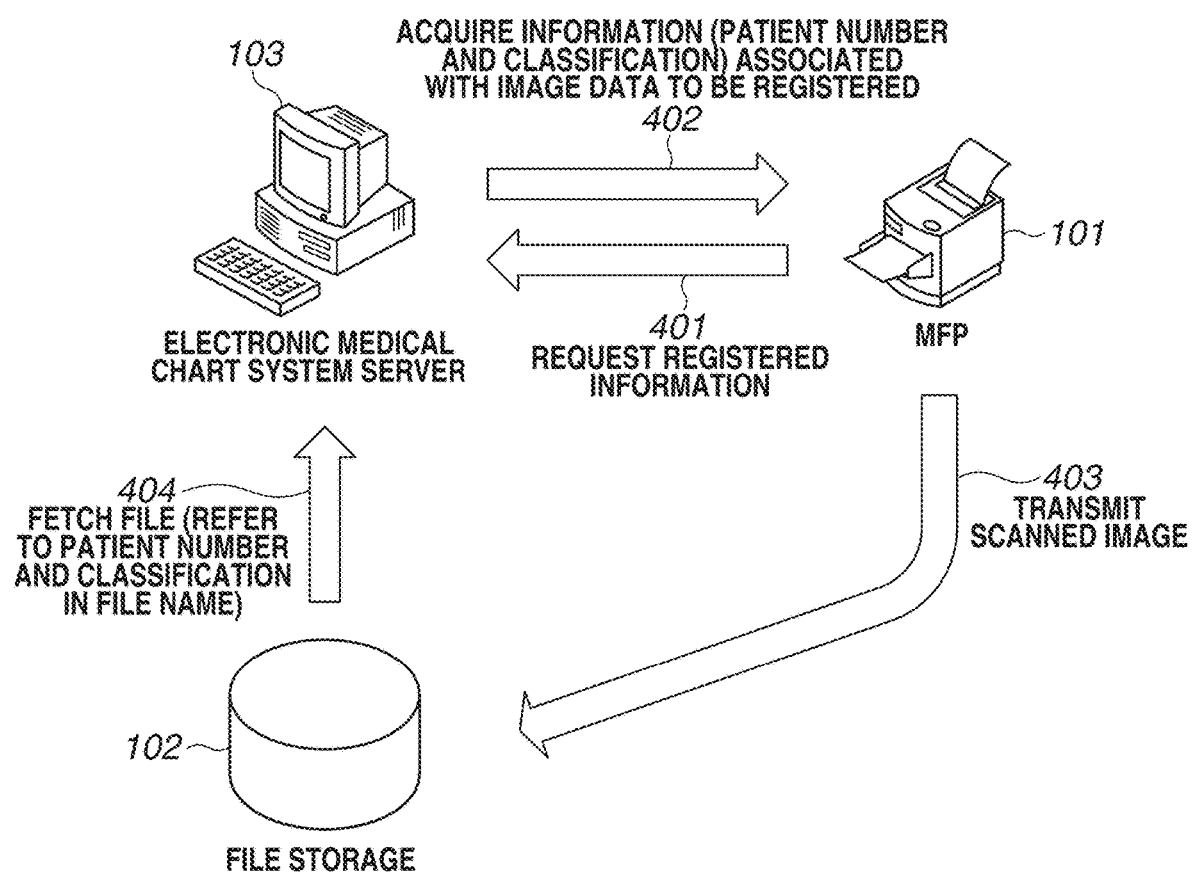
FIG. 4 illustrates an example of cooperation among the image forming apparatus, a file storage, and an electronic medical chart system server.

FIG. 4 illustrates an example of cooperation among the image forming apparatus 101, the file storage 102, and the electronic medical chart system server 103.

If the electronic medical chart cooperation button 303 is pressed, the image forming apparatus 101 requests acquisition of information to be associated with image data to be registered from the electronic medical chart system as processing 401. The electronic medical chart system server 103 transmits a patient number, a patient name, a treatment status, and classification information to the image forming apparatus 101 as processing 402. Subsequently, the image forming apparatus 101 transmits the image data generated therein to the file storage 102 as illustrated in processing 403. The electronic medical chart system server 103 can refer to a file stored in the file storage 102 as illustrated in processing 404.

The timing of the processing 401 for acquiring the information to be associated with the image data is not limited to a timing at which the electronic medical chart cooperation button 303 is selected. The processing 401 may be performed, for example, at a time of start-up of the image forming apparatus 101, at a time of restoring from a power saving state, and at a periodic timing.

FIG. 5 illustrates an example of a patient information database (DB) and classification information in the electronic medical chart system server 103.

A patient information DB 501 is a database that is updated in the electronic medical chart system server 103 at a timing of patient registration, reception, hospitalization registration, accounting, and the like. Examples of the patient information including a patient number, a patient name, a patient condition, a clinical department, an address, and a point of contact are managed in the database.

Classification information 502 is classification information of a document managed for each patient by the electronic medical chart system server 103. Examples of the classification information of the document include a medical questionnaire, a referral form, a health insurance card, a medication chart, and a medical certificate.

FIGS. 6A to 6D illustrate examples of an execution screen of an electronic medical chart cooperation application that is executed in a case where the electronic medical chart cooperation button 303 is pressed.

FIG. 6A illustrates a patient selection screen displayed in a case where the electronic medical chart cooperation button 303 is pressed, and patients are displayed in a list. A screen title 601 is an area in which a name of a screen being displayed, which is "patient selection", is displayed.

In patient list selection buttons 602, buttons of, for example, "all", "outpatient (new)", "outpatient (current day)", "hospitalization", and "paid" are displayed, and a patient list is displayed for each treatment status of patients. A button name to be displayed in the patient list selection button 602 may be displayed based on information indicating the treatment status received from the electronic medical chart system server 103. FIG. 6B illustrates a patient list screen in a case where the "outpatient (new)" is selected in the patient list selection buttons 602. FIG. 6C illustrates a patient list screen in a case where the "outpatient (current day)" is selected in the patient list selection buttons 602. FIG. 6D illustrates a patient list screen in a case where the "paid" is selected in the patient list selection buttons 602.

Items 603 is a list display for selecting a patient to be associated with a document to be read. The patient information displayed as a list may be acquired by communicating with the electronic medical chart system server 103, or may use data stored in the storage 114 or the file storage 102 in the image forming apparatus 101. If a user presses an item in the list, the patient information of the pressed item is stored as the patient information to be assigned to an image file, and the screen shifts to a classification selection screen illustrated in FIG. 7. If the user slides the items 603 while pressing the item, the displayed patient information is scrolled, and the patient information that has not been displayed is displayed. According to the present exemplary embodiment, a patient number 604, a patient name 605, and a treatment status 606 are displayed for each patient in the items 603, but other information included in the patient information may be displayed. A scroll bar 607 displays a position of the patient information displayed in the items 603 in the list, and the list display can be scrolled by pressing and sliding the scroll bar 607 or pressing a scroll button on top or bottom.

Figure 7:
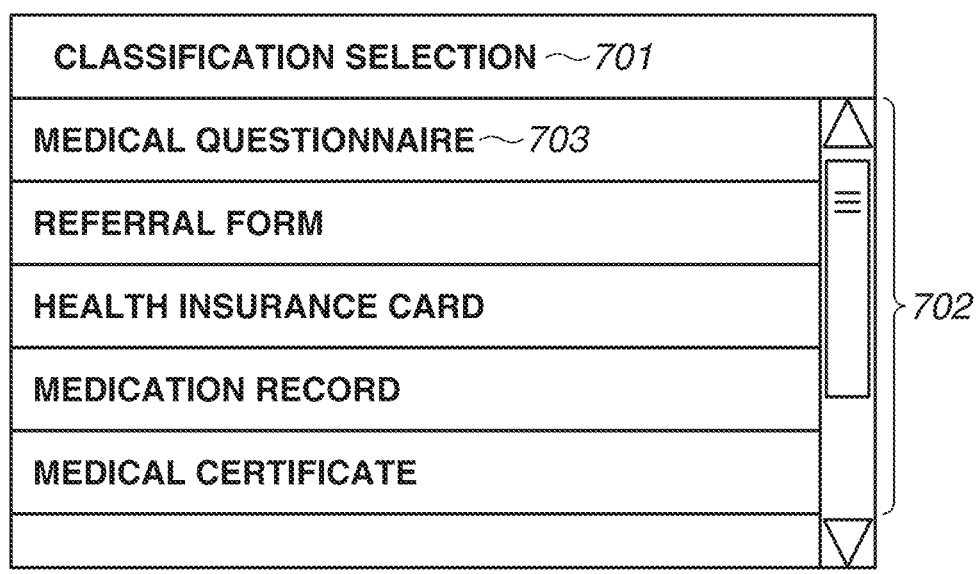
FIG. 7 illustrates an example of a document classification selection screen of the electronic medical chart cooperation application.

FIG. 7 illustrates an example of the classification selection screen of the electronic medical chart cooperation application. A screen title 701 is an area in which a name of a screen being displayed, which is "classification selection", is displayed. A classification list display 702 is a list display for selecting document classification to be associated with the image data generated by reading the document. Document classification information displayed as a list may be acquired by communicating with the electronic medical chart system server 103, or may use data stored in the storage 114 or the file storage 102 in the image forming apparatus 101. If a user presses an item in the list, the image forming apparatus 101 stores the classification information of the pressed item as the classification information to be assigned to an image file, reads the document, then generates an image file, and transmits the image file to the file storage 102. If the user slides the classification list display 702 while pressing the classification list display 702, the displayed classification information is scrolled, and the classification information which has not been displayed is displayed. A classification name 703 is a classification name to be associated with a document when being pressed. A read setting in reading the document and destination information of the file storage can be set as an application setting. Further, a folder name in the file storage 102 to be a destination may be a folder name unique to the electronic medical chart system set in the application setting, or may be determined from the patient information selected in the screens illustrated in FIGS. 6A to 6D.

Figure 8:
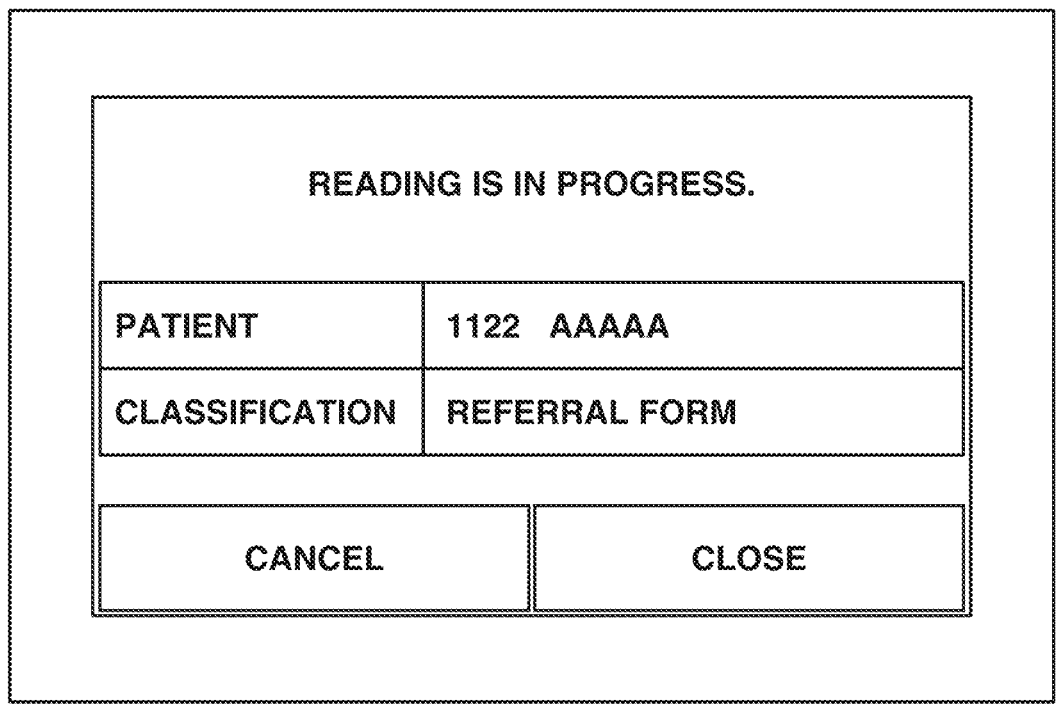
FIG. 8 illustrates an example of a screen during a document reading.

FIG. 8 illustrates an example of a screen during the reading of a document. In a reading-in-progress screen, the patient information and the classification information of the document selected in the screens illustrated in FIGS. 6A to 6D and FIG. 7 are displayed on the operation unit 118. In the example in FIG. 8, reading of the document is executed in a state in which "1122 AAAAA" and "referral form" are respectively selected as the patient information and the classification. The patient information includes the patient number "1122" and the patient name "AAAAA".

Figure 9:
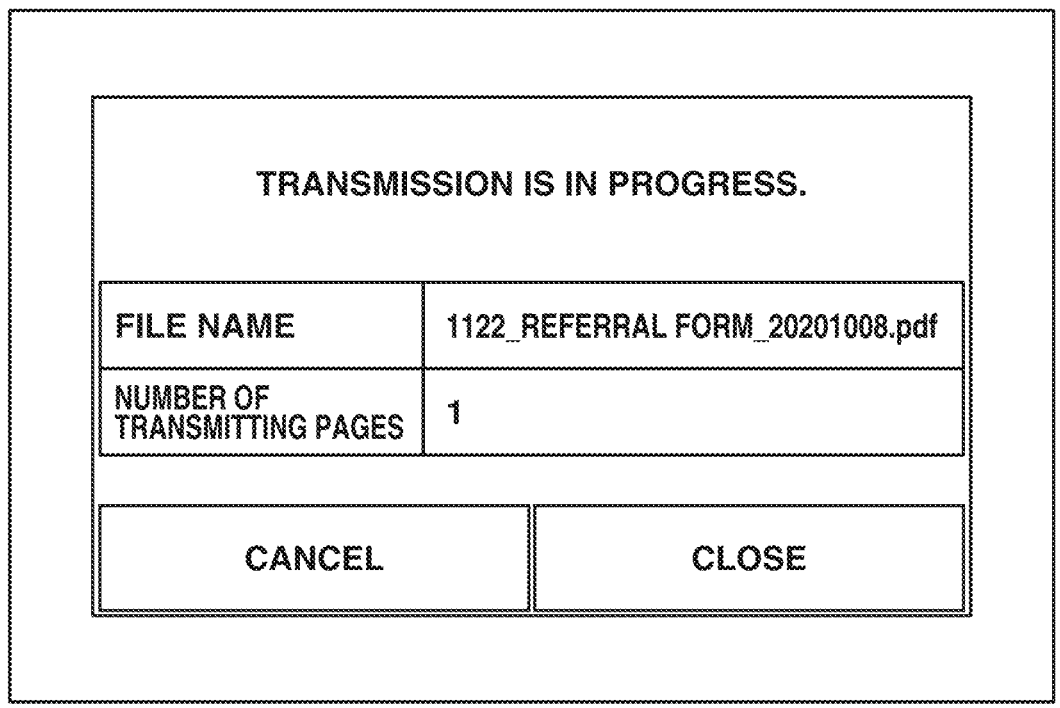
FIG. 9 illustrates an example of a screen during an image data transmission.

FIG. 9 illustrates an example of a screen during the transmitting of the image data. In a transmission-in-progress screen of the image data, a file name, and the number of transmitting pages are displayed on the operation unit 118. In the example in FIG. 9, "1122 AAAAA" and "referral form" are respectively selected as the patient information and the classification as with FIG. 8, so that the patient information and the classification information are each added to the file name like the file name "1122_referral form_20201008.pdf". If the screen in FIG. 8 is displayed, and reading of the document is completed, then the screen illustrated in FIG. 9 is displayed.

Figure 10:
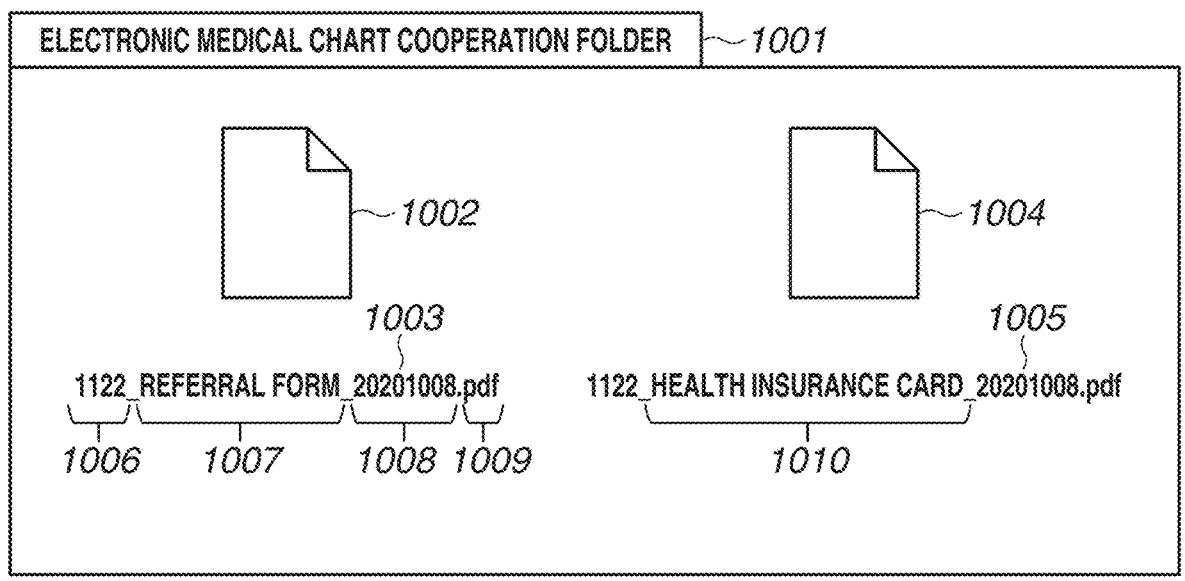
FIG. 10 illustrates an example of a transmission destination folder after the execution of the electronic medical chart cooperation application.

FIG. 10 illustrates an example of a transmission destination folder after executing the electronic medical chart cooperation application. FIG. 10 illustrates a content in the file storage 102 after "1122 AAAAA" is selected in the screens in FIGS. 6A to 6D, and the image data generated by selecting "referral form" in the screen in FIG. 7 and reading an image of the document is transmitted.

A folder 1001 is stored in the file storage 102. A file 1002 is an image file that has been generated after first reading of the document by the image forming apparatus 101, and such a state is regarded as a registered state. A file name 1003 is a name of the file 1002. An image file 1004 is an image file that has been generated after second reading of the document, and a file name 1005 is a name of the image file 1004. The file name 1003 will now be described in detail. A patient number 1006 is the patient number of the patient selected in the screens in FIGS. 6A to 6D, and "1122" is input. Classification information 1007 is the classification of the document selected in the screen illustrated in FIG. 7, and "referral form" is input. According to the present exemplary embodiment, the classification name of the document classification displayed in the screen in FIG. 7 is added as it is, but a character string different from a character string for display associated with the document classification may be added. A date 1008 is a date when the document is read that is automatically added to the file name, and indicates information of a previously registered time.

Information about a user who executes reading and other information may be automatically added to the file name, or whether to add the information may be set as the application setting. An extension 1009 is an extension indicating a type of the file and is determined by the read setting of the application.

The file name 1005 is different from the file name 1003 only in classification 1010 of the document that has been reselected.

Figure 11:
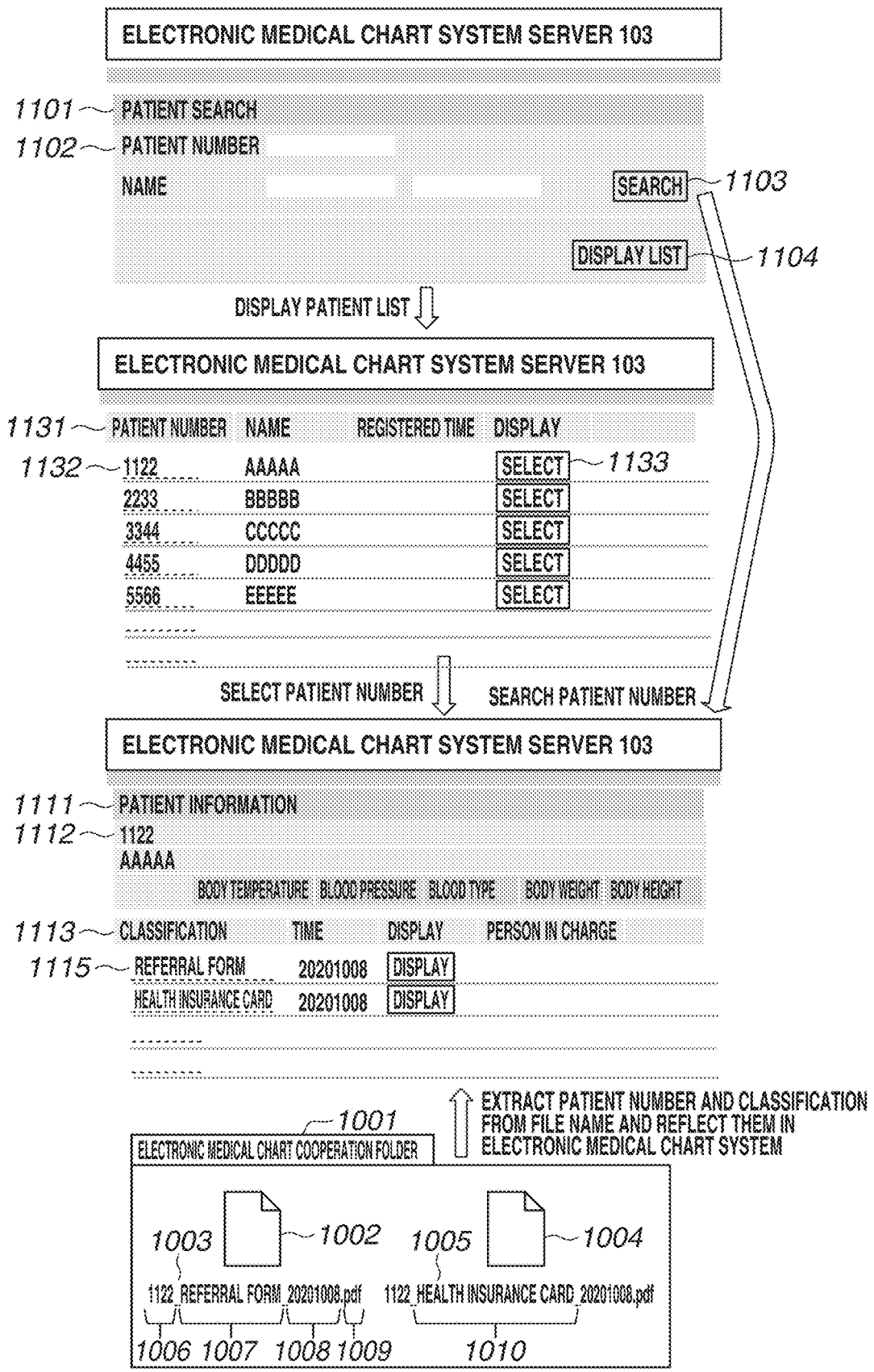
FIG. 11 illustrates an example of cooperation between contents of the file storage and the electronic medical chart system server.

FIG. 11 illustrates an example of cooperation between the contents of the file storage 102 and the electronic medical chart system server 103.

The electronic medical chart system server 103 includes a patient search screen 1101 as a method for confirming a registered patient. The patient search screen 1101 includes a search button 1103 for performing a search based on the patient number input in an input field 1102 and a list display button 1104 for displaying patient numbers in a list.

In a case where the list display button 1104 is pressed, the patient search screen 1101 transitions to a list display screen 1131. In the list display screen 1131, a file stored in the folder 1001 and obtained by extracting the patient number 1006 is displayed in an item 1132.

In a case where a selection button 1133 is pressed, the list display screen 1131 transitions to a patient information screen 1111, which is an information screen of the patient associated with the patient number displayed in the item 1132. As a different method for displaying the patient information screen 1111, the screen also transitions by inputting the patient number of the patient to the input field 1102 in the patient search screen 1101 and pressing the search button 1103.

The patient information screen 1111 displays a list of files in which a patient number 1122 matches the patient number 1006 in the file name among the files stored in the file storage 102. The patient information screen 1111 displays classification information 1113 of the document by extracting the classification information 1113 from the classification information included in the file name of the file. For example, a referral form 1115 is extracted from the classification information 1007 included in the file name 1003 of the file 1002 and displayed. Further, a registered time of the referral form 1115 is extracted from the date 1008 included in the file name 1003 of the file 1002 and displayed.

In other words, the electronic medical chart system server 103 determines a distribution destination of the image file based on the file name of the image file received from the file storage 102.

Figure 12:
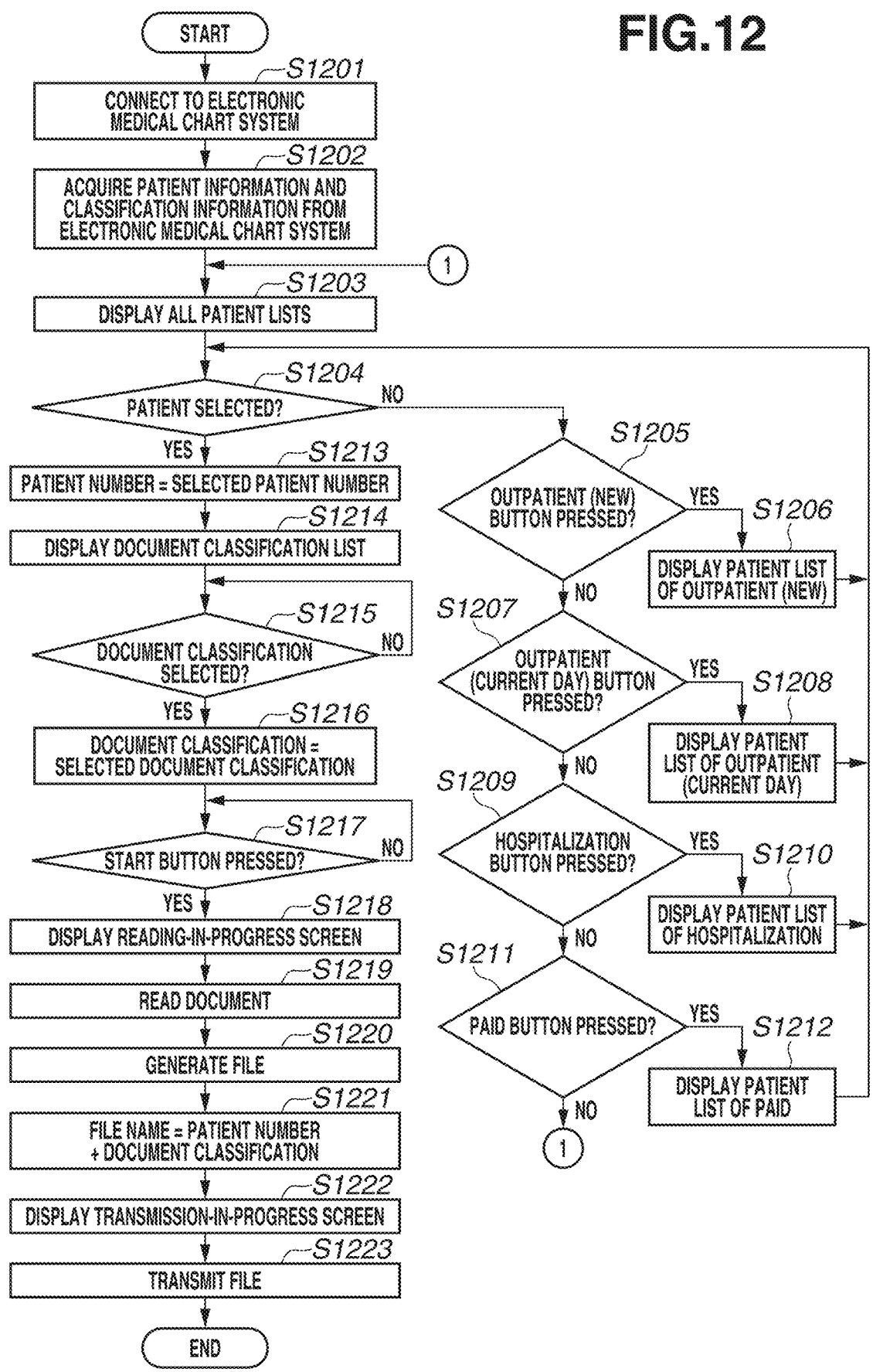
FIG. 12 is a flowchart illustrating an example of patient selection list display processing by the electronic medical chart cooperation application.

FIG. 12 is a flowchart illustrating an example of patient selection list display processing performed by the electronic medical chart cooperation application. The present processing starts if the electronic medical chart cooperation button 303 is pressed in the image forming apparatus 101.

In S1201, the CPU 111 connects to the electronic medical chart system server 103 via the communication unit IN 123, and the processing proceeds to S1202.

In S1202, the CPU 111 receives the patient information and a document classification list from the electronic medical chart system server 103 via the communication unit IN 123, and the processing proceeds to S1203. The time when the processing 401 for acquiring the patient information and the document classification list is not limited to the time of transmitting the image data. The processing 401 may be performed at the time of start-up of the image forming apparatus 101, at the time of restoring from the power saving state, or at a periodic timing.

In S1203, the CPU 111 displays the patient list included in the patient information received from the electronic medical chart system server 103 on the operation unit 118 (FIG. 6A), and the processing proceeds to S1204.

In S1204, the CPU 111 determines whether a patient is selected from the patient list displayed on the operation unit 118. In a case where a patient is selected (YES in S1204), the processing proceeds to S1213. In a case where a patient is not selected (NO in S1204), the processing proceeds to S1205.

In S1205, the CPU 111 determines whether the outpatient (new) button is pressed in the patient list selection buttons 602. In a case where the outpatient (new) button is pressed (YES in S1205), the processing proceeds to S1206. In a case where the outpatient (new) button is not pressed (NO in S1205), the processing proceeds to S1207.

In S1206, the CPU 111 displays the patient list of which the treatment status is the outpatient (new) based on the patient information acquired from the electronic medical chart system server 103 (FIG. 6B), and the processing proceeds to S1204.

In S1207, the CPU 111 determines whether the outpatient (current day) button is pressed in the patient list selection buttons 602. In a case where the outpatient (current day) button is pressed (YES in S1207), the processing proceeds to S1208. In a case where the outpatient (current day) button is not pressed (NO in S1207), the processing proceeds to S1209.

In S1208, the CPU 111 displays the patient list of which the treatment status is the outpatient (current day) based on the patient information acquired from the electronic medical chart system server 103 (FIG. 6C), and the processing proceeds to S1204.

In S1209, the CPU 111 determines whether the hospitalization button is pressed in the patient list selection button 602. In a case where the hospitalization button is pressed (YES in S1209), the processing proceeds to S1210. In a case where the hospitalization button is not pressed (NO in S1209), the processing proceeds to S1211.

In S1210, the CPU 111 displays the patient list of which the treatment status is the hospitalization based on the patient information acquired from the electronic medical chart system server 103, and the processing proceeds to S1204.

In S1211, the CPU 111 determines whether the paid button is pressed in the patient list selection button 602. In a case where the paid button is pressed (YES in S1211), the processing proceeds to S1212. In a case where the paid button is not pressed (NO in S1211), the processing returns to S1203.

In S1212, the CPU 111 displays the patient list of which the treatment status is paid based on the patient information acquired from the electronic medical chart system server 103 (FIG. 6D), and the processing proceeds to S1204.

In S1213, the CPU 111 stores the selected patient number in the RAM 113 as the patient information to be added to an image file, and the processing proceeds to S1214.

In S1214, the CPU 111 displays the document classification list from the classification of the document acquired from the electronic medical chart system server 103 on the operation unit 118 (FIG. 7), and the processing proceeds to S1215.

In S1215, the CPU 111 determines whether the classification of the document is selected from the displayed document classification list. In a case where the classification of the document is selected (YES in S1215), the processing proceeds to S1216.

In S1216, the CPU 111 stores the classification of the document selected in S1215 in the RAM 113 as the classification information of the document to be added to the image file.

In S1217, the CPU 111 detects whether a read start button is pressed. In a case where pressing of the start button by a user is detected (YES in S1217), the processing proceeds to S1218.

In S1218, the CPU 111 displays the reading-in-progress screen on the operation unit 118 (FIG. 8), and the processing proceeds to S1219.

In S1219, the reading unit 116 reads the document, and the processing proceeds to S1220.

In S1220, the CPU 111 generates an image file from the document read in S1219, and the processing proceeds to S1221.

In S1221, the CPU 111 determines a file name based on the patient number and the document classification stored in S1213 and S1216 and assigns the file name to the image file generated in S1220. The patient number and the document classification may be written in tag information or header information of the image file. The processing then proceeds to S1222.

In S1222, the CPU 111 displays the transmission-in-progress screen on the operation unit 118 (FIG. 9), and the processing proceeds to S1223.

In S1223, the CPU 111 transmits the image file to the file storage 102 via the network 100. After the image file is transmitted, the present processing is terminated.

In a second exemplary embodiment, an example will be described in which buttons which are sorted for each patient attribute in advance are displayed on a home screen.

Figure 13:
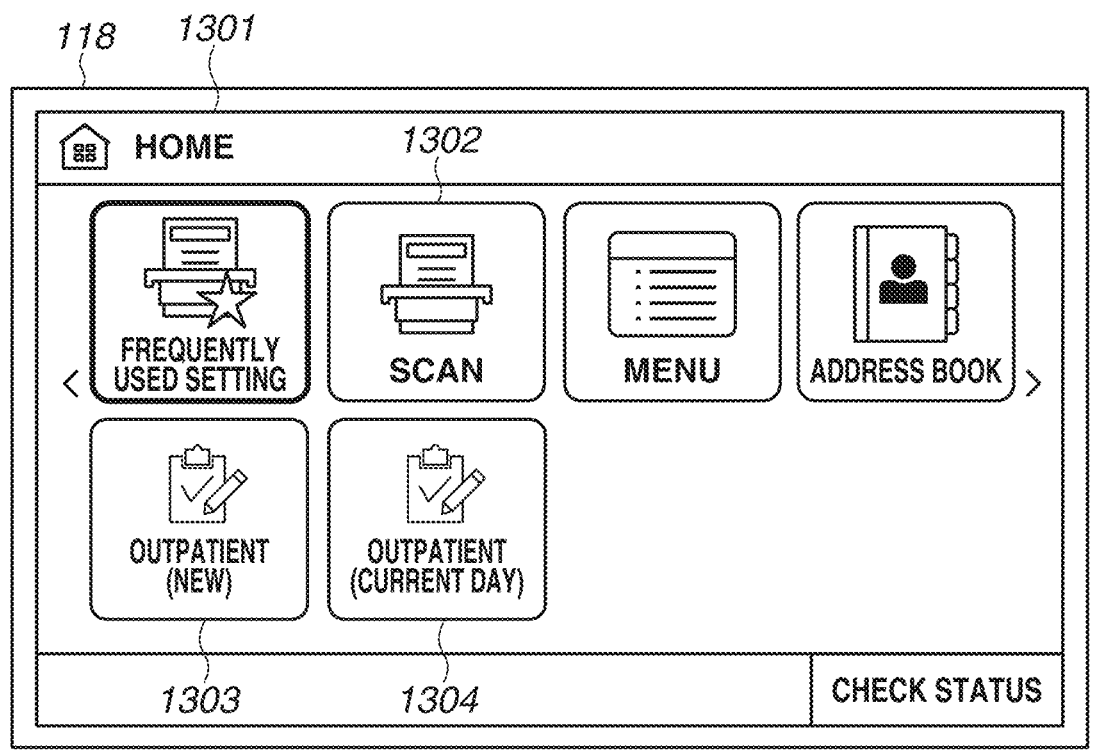
FIG. 13 illustrates an example of a home screen that is displayed immediately after start-up of the image forming apparatus.

FIG. 13 illustrates an example of a home screen that is displayed immediately after start-up of the image forming apparatus 101. The home screen is a screen for instructing execution of each function of the image forming apparatus 101 and is displayed on a touch panel screen included in the operation unit 118. In the home screen, touch images of respective functions, such as "frequently used setting", "scan", "menu", and "address book", executed by the image forming apparatus 101 are displayed. A screen name 1301 is an area in which a name of a current screen is displayed, and a name "home" is displayed. A function button 1302 is a button for executing each function provided in the image forming apparatus 101, and a corresponding function is executed if the button is pressed. One of function button pages in which a plurality of the function buttons 1302 is arranged is displayed on the screen.

An outpatient (new) button 1303 of the electronic medical chart cooperation is a button for selecting a patient from the patient list of the outpatient (new), reading a referral form and a medical questionnaire, and storing the read data in the file storage 102.

An outpatient (current day) button 1304 of the electronic medical chart cooperation is a button for selecting a patient from the patient list of the outpatient (current day), reading a referral form and a medical questionnaire, and storing the read data in the file storage 102.

FIGS. 14A and 14B illustrate examples of a patient selection screen of the electronic medical chart cooperation application.

FIG. 14A illustrates the patient selection screen that is executed in a case where the outpatient (new) button 1303 of the electronic medical chart cooperation is pressed, and a patient of the outpatient (new) is displayed in a list.

FIG. 14B illustrates the patient selection screen that is executed in a case where the outpatient (current day) button 1304 of the electronic medical chart cooperation is pressed, and a patient of the outpatient (current day) is displayed in a list.

Figure 15:
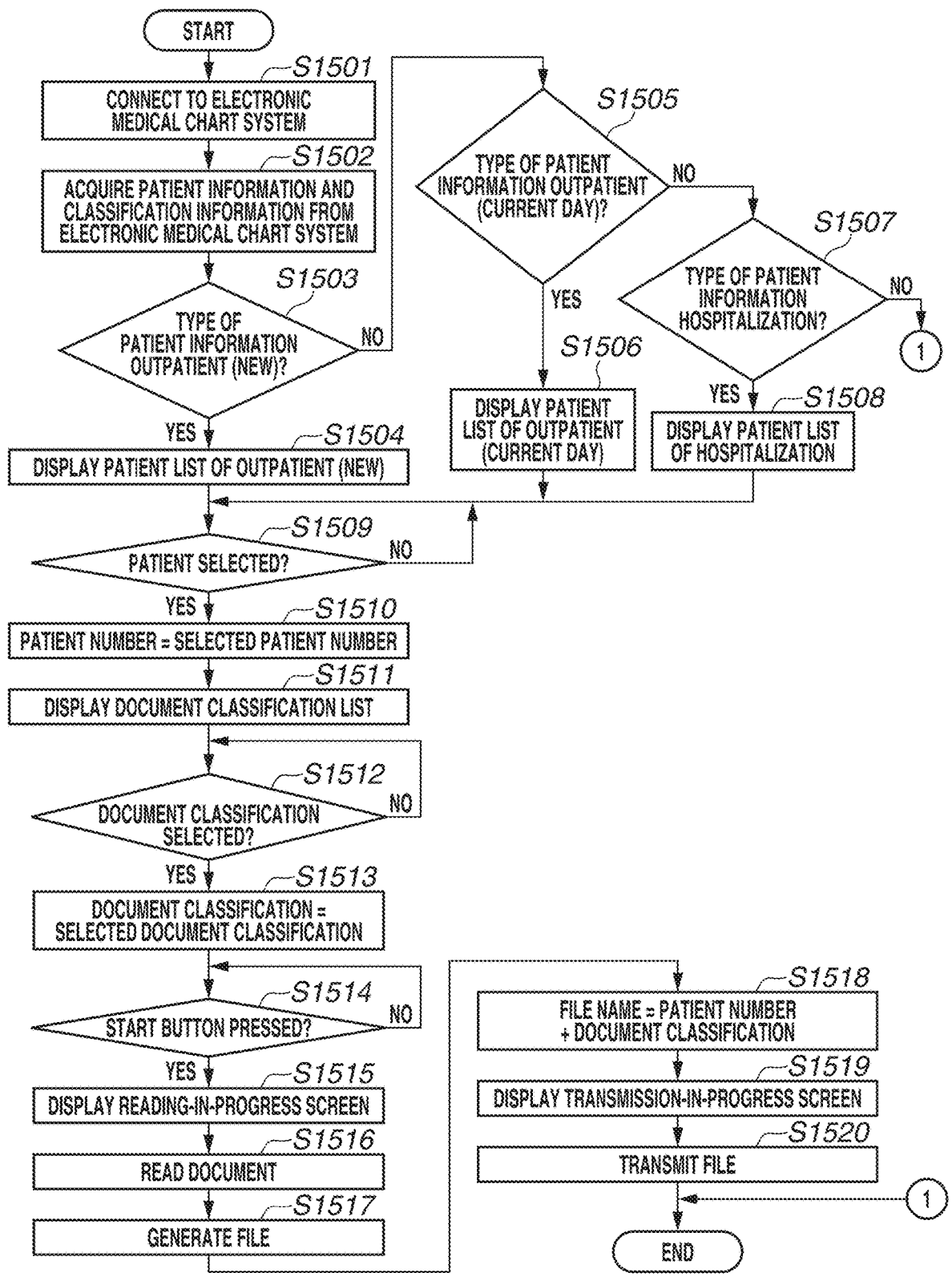
FIG. 15 is a flowchart illustrating an example of patient selection list display processing by the electronic medical chart cooperation application.

FIG. 15 is a flowchart illustrating an example of patient selection list display processing of the electronic medical chart cooperation application. The present processing is started if the outpatient (new) button 1303 or the outpatient (current day) button 1304 of the electronic medical chart cooperation is pressed in the image forming apparatus 101.

In S1501, the CPU 111 connects to the electronic medical chart system server 103.

The processing then proceeds to S1502.

In S1502, the CPU 111 receives the patient information and the document classification list from the electronic medical chart system server 103, and the processing proceeds to S1503. The time when the processing 401 for acquiring the patient information and the document classification list is not limited to the time of transmitting the image data. The processing 401 may be performed at the time of start-up of the image forming apparatus 101, at the time of restoring from the power saving state, or at a regular timing.

In S1503, the CPU 111 determines whether the outpatient (new) button 1303 of the electronic medical chart cooperation is pressed. In a case where the outpatient (new) button is pressed (YES in S1503), the processing proceeds to S1504. In a case where the outpatient (new) button is not pressed (NO in S1503), the processing proceeds to S1505.

In S1504, the CPU 111 displays the patient list of which the treatment status is the outpatient (new) based on the patient information acquired from the electronic medical chart system server 103 on the operation unit 118 (FIG. 14A). The processing then proceeds to S1509.

In S1505, the CPU 111 determines whether the outpatient (current day) button 1304 of the electronic medical chart cooperation is pressed. In a case where the outpatient (current day) button is pressed (YES in S1505), the processing proceeds to S1506. In a case where the outpatient (current day) button is not pressed (NO in S1505), the processing proceeds to S1507.

In S1506, the CPU 111 displays the patient list of which the treatment status is the outpatient (current day) based on the patient information acquired from the electronic medical chart system server 103 on the operation unit 118 (FIG. 14B). The processing then proceeds to S1509.

In S1507, the CPU 111 determines whether the hospitalization button of the electronic medical chart cooperation is pressed. In a case where the hospitalization button is pressed (YES in S1507), the processing proceeds to S1508. In a case where the hospitalization button is not pressed (NO in S1507), the present processing is terminated.

In S1508, the CPU 111 displays the patient list of which the treatment status is the hospitalization based on the patient information acquired from the electronic medical chart system server 103. The processing then proceeds to S1509.

In S1509, the CPU 111 determines whether a patient is selected from the patient list.

In a case where a patient is selected (YES in S1509), the processing proceeds to S1510.

In S1510, the CPU 111 stores the selected patient number as the patient information to be added to an image file, and the processing proceeds to S1511.

In S1511, the CPU 111 displays the document classification list from the classification of the document acquired from the electronic medical chart system server 103 (FIG. 7). The processing then proceeds to S1512.

In S1512, the CPU 111 determines whether the classification of the document is selected from the document classification list. In a case where the classification of the document is selected (YES in S1512), the processing proceeds to S1513.

In S1513, the CPU 111 stores the classification of the document selected in S1512 in the RAM 113 as the classification information of the document to be added to the image file.

In S1514, the CPU 111 detects whether the read start button is pressed. In a case where pressing of the start button by a user is detected (YES in S1514), the processing proceeds to S1515.

In S1515, the CPU 111 displays the reading-in-progress screen on the operation unit 118 (FIG. 8), and the processing proceeds to S1516.

In S1516, the reading unit 116 reads the document, and the processing proceeds to S1517.

In S1517, the CPU 111 generates an image file from the document read in S1516, and the processing proceeds to S1518.

In S1518, the CPU 111 determines a file name based on the patient number and the document classification stored in S1510 and S1513 and assigns the file name to the image file generated in S1517. The patient number and the document classification may be written in tag information or header information of the image file. The processing then proceeds to S1519.

In S1519, the CPU 111 displays the transmission-in-progress screen on the operation unit 118 (FIG. 9), and the processing proceeds to S1520.

In S1520, the CPU 111 transmits the image file to the file storage 102 via the network 100. After the image file is transmitted, the present processing is terminated. As described above, according to the present exemplary embodiment, the image forming apparatus downloads the patient information and the classification information of the document from the electronic medical chart system. The image forming apparatus thereby does not need to set a lot of the patient information and the classification information of the documents in advance and to reset the patient information that changes from day to day.

The patient and the classification of the document are respectively selected from the list in the downloaded patient information, and a file is transmitted by adding the selected content to the file name, so that the document can be easily registered in the electronic medical chart system of the transmission destination. The patient list display can also be selected based on the treatment status of the patient, and thus the patient can be easily selected.

According to a third exemplary embodiment, an example is described in which the same image file is prevented from being redundantly registered in the electronic medical chart system by confirming information about the image file registered in the electronic medical chart system from the image forming apparatus 101.

FIG. 16 illustrates an example of a document classification selection screen at the time of preventing a double registration. In a case where the document classification information to be displayed in a list is acquired, if the document is already stored, the stored classification information may be displayed in a gray-out state as illustrated in an item 1603. Further, if the document is already stored, a display name may be changed as illustrated in an item 1604 from a name of the acquired document classification information.

The document classification that is not registered is differentiated by the above-described change of the display, and thereby a fact that the document is already stored can be confirmed on the screen.

In a case where a user presses the item 1603 in the list, the screen transitions to a screen 1610 displaying that the selected document is stored.

In a case where a YES button 1611 is pressed, the document is read, and then an image file is generated and transmitted to the file storage 102. In a case where a NO button 1612 is pressed, the document is not read, and the screen shifts to a screen 1601.

In a case where a user presses the item 1603 in the list, and the selected document is prohibited from retransmission, the screen shifts to a screen 1620. In a case where an OK button 1621 is pressed, the document is not read, and the screen shifts to the screen 1601.

In a case where the document classification information is acquired, the document classification information including previously transmitted information may be acquired, and in a case where a certain period of time has passed from the tome of the previous transmission of information to a time of current transmission, gray-out processing may not be performed.

FIG. 17 illustrates an example of the document classification information to be acquired by communicating with the electronic medical chart system server 103. An acquired list 1700 includes a patient number 1701 and document classification 1702, and previously registered time 1703 is added to the list as information for determining whether the information is already registered. In a case where a time is set in the previously registered time 1703, it indicates a registered state. In a case where the time is not set as in an item 1711, it indicates an unregistered state.

Further, the list 1700 includes information 1704 for determining whether re-registration is permitted and information 1705 indicating a time when re-registration can be performed.

Figure 18:
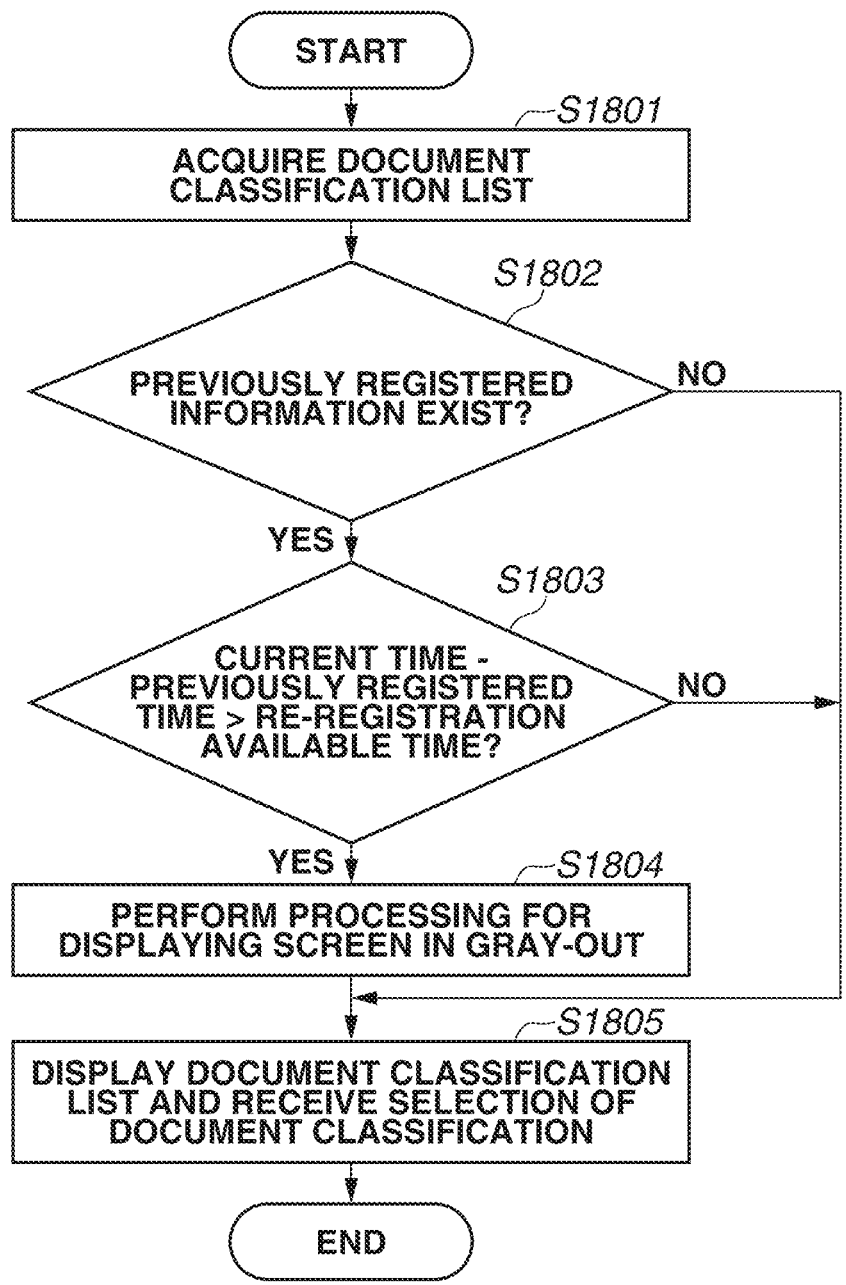
FIG. 18 is a flowchart illustrating an example of processing for displaying the document classification selection screen illustrated in FIG. 16.

FIG. 18 is a flowchart illustrating an example of processing for displaying the screen 1601 in FIG. 16.

In S1801, the CPU 111 receives the document classification list from the electronic medical chart system server 103.

In S1802, the CPU 111 determines whether the previously registered information exists in the acquired document classification list. In a case where the previously registered information exists (YES in S1802), the processing proceeds to S1803. In a case where the previously registered information does not exist (NO in S1802), the processing proceeds to S1805.

In S1803, the CPU 111 calculates a difference between the previously registered time and a current time. In a case where the difference exceeds a re-registration available time (YES in S1803), the processing proceeds to S1804. In a case where the difference does not exceed the re-registration available time (NO in S1803), the processing proceeds to S1805.

In S1804, the CPU 111 performs processing for displaying the document classification including the previously registered information in gray-out.

In S1805, the CPU 111 displays the screen 1601 of the document classification list acquired in S1801 on the operation unit 118 and receives selection of the document classification from a user.

Figure 19:
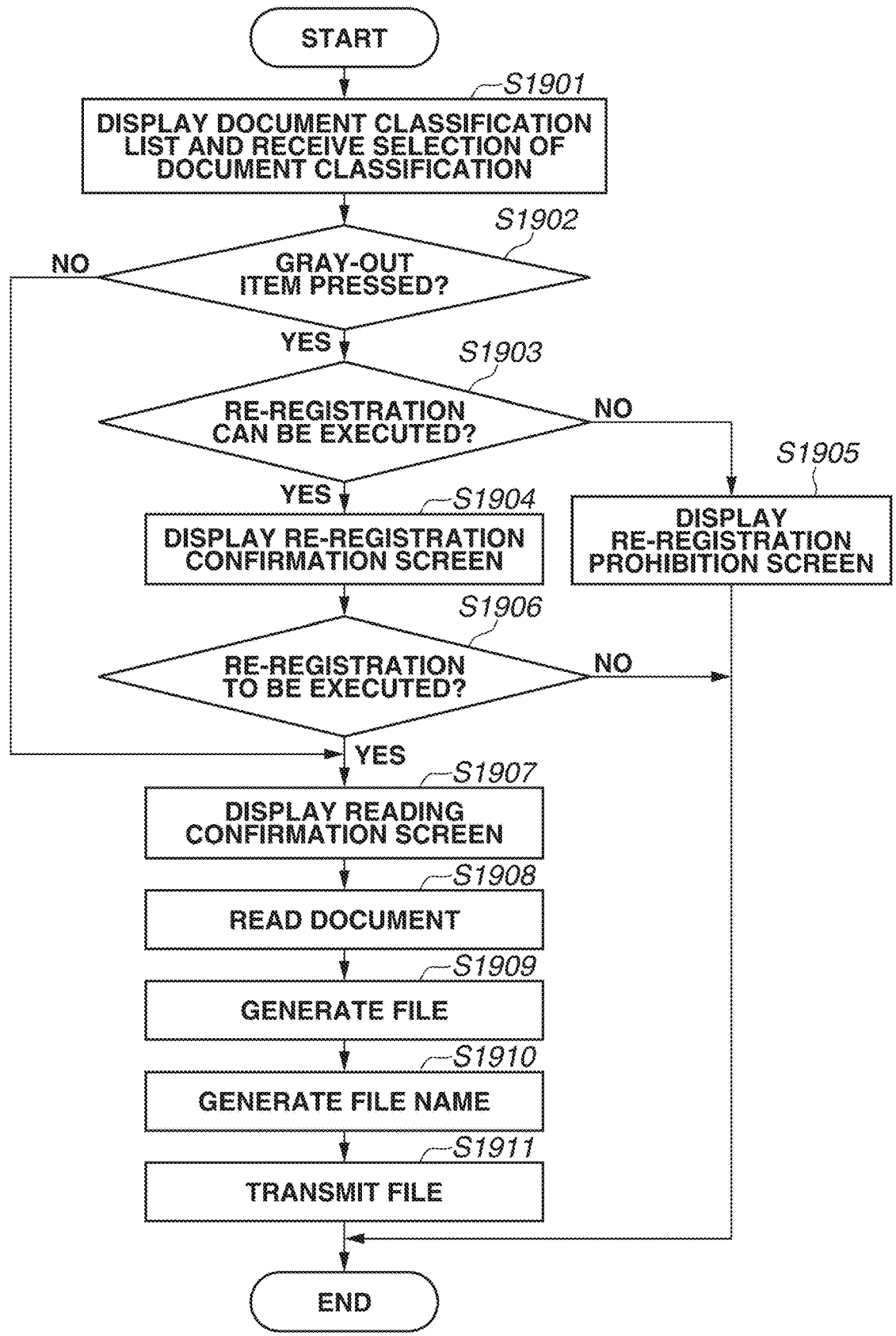
FIG. 19 is a flowchart illustrating an example of processing for displaying HOME screens illustrated in FIG. 16.

FIG. 19 is a flowchart illustrating an example of processing for displaying the screen 1610 and the screen 1620 illustrated in FIG. 16.

In S1901, the CPU 111 displays the document classification list acquired from the electronic medical chart system server 103 and the state in which the processing in the flowchart in FIG. 18 is performed.

In S1902, the control unit 110 determines whether the item displayed in gray-out is pressed in the screen displayed on the operation unit 118. In the case where the gray-out item is pressed (YES in S1902), the processing proceeds to S1903. In the case where the gray-out item is not pressed (NO in S1902), the processing proceeds to S1907.

In S1903, the CPU 111 checks the information 1704 in FIG. 17 in addition to the item selected in S1902 to determine whether the re-registration can be executed. In a case where the re-registration can be executed (YES in S1903), the processing proceeds to S1904. In a case where the re-registration cannot be executed (NO in S1903), the processing proceeds to S1905.

In S1904, the CPU 111 displays the screen 1610 for confirming re-registration illustrated in FIG. 16 on the operation unit 118, and then the processing proceeds to S1906.

In S1905, the CPU 111 displays the screen 1620 for prohibiting re-registration illustrated in FIG. 16 on the operation unit 118. In a case where pressing of the OK button 1621 by a user is detected, the processing in the present flowchart is terminated.

In S1906, the CPU 111 receives selection on the screen 1610 for confirming re-registration in FIG. 16 by the user. In a case where pressing of the YES button 1611 is detected (YES in S1906), the processing proceeds to S1907. In a case where pressing of the NO button 1612 is detected (NO in S1906), the processing in the present flowchart is terminated.

In S1907, the CPU 111 detects whether the read start button is pressed. In a case where pressing of the start button by the user is detected, the processing proceeds to S1908.

In S1908, the reading unit 116 reads an image of the document. In S1909, the CPU 111 generates an image file based on the image of the document read in S1908.

In S1910, the CPU 111 determines a file name based on the patient number selected in the screen illustrated in FIG. 6A and the document classification selected in the screen illustrated in FIG. 16 and assigns the file name to the image file generated in S1909.

The patient number and the document classification may be written in tag information or header information of the image file.

In 51911, the CPU 111 transmits the image file to the file storage 102 via the network 100.

As described above, according to the present exemplary embodiment, a file which is already registered is indicated before executing reading of a document, and thereby an erroneous operation, such as redundant registration, can be prevented.

OTHER EMBODIMENTS

Some embodiment(s) of the present disclosure can also be realized by a computer of a system or apparatus that reads out and executes computer-executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer-executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer-executable instructions. The computer-executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has described exemplary embodiments, it is to be understood that some embodiments are not limited to the disclosed exemplary embodiments. The scope of the following claims is to be accorded the broadest interpretation so as to encompass all such modifications and equivalent structures and functions.

This application claims priority to Japanese Patent Application No. 2021-069802, which was filed on Apr. 16, 2021 and which is hereby incorporated by reference herein in its entirety.

What is claimed is:

1. An image processing apparatus comprising:
a scanner;
a communicator that receives patient information and category information of a document from an information processing apparatus; and
a controller;
wherein the controller receives selection of patient information from the received patient information by a user,
wherein the controller displays, in response to the selection of the patient information, the category information on a display,
wherein the controller receives selection of category information from the displayed category information and a scan instruction by the user,
wherein the controller displays, in a grayout state, category information in which an image file is registered and for which a predetermined period has not elapsed from registration of the image file,
wherein the controller displays, in a non-grayout state, category information in which an image file is registered and for which the predetermined period has elapsed from registration of the image file,
wherein the scanner scans, based on the scan instruction, an image of a document and generates an image file and then the controller determines, based on the selected patient information and the selected category information, a file name of the image file, the determined file name including the selected patient information and the selected category information, and
wherein the communicator transmits the generated image file to a server.

2. The image processing apparatus according to claim 1, wherein the controller displays the selected patient information and the selected category information on the display while the scanner scans the image of the document.

3. The image processing apparatus according to claim 1, wherein the controller displays a confirmation screen for confirming whether to scan the image of the document in a case where an image file corresponding to the selected patient information and the selected category information has already been stored.

4. The image processing apparatus according to claim 1, wherein the server transmits the transmitted image file to the information processing apparatus, and the information processing apparatus determines a distribution destination of the image file based on the file name of the image file received from the server.

5. The image processing apparatus according to claim 1, wherein the communicator receives the patient information from the information processing apparatus based on a predetermined instruction given by the user on the image processing apparatus.

6. The image processing apparatus according to claim 1, wherein the patient information is ID of a patient.

7. A method of controlling an image processing apparatus, the method comprising:
- receiving patient information and category information of a document from an information processing apparatus;
- receiving selection of patient information from the received patient information by a user;
- displaying, in response to the selection of the patient information, the category information on a display;
- receiving selection of category information from the displayed category information and a scan instruction by the user;
- wherein category information in which an image file is registered and for which a predetermined period has not elapsed from registration of the image file is displayed in a grayout state,
- wherein category information in which an image file is registered and for which the predetermined period has elapsed from registration of the image file is displayed in a non-grayout state,
- scanning, based on the scan instruction, an image of a document and generating an image file and then determining, based on the selected patient information and the selected category information, a file name of the image file, the determined file name including the selected patient information and the selected category information; and
- transmitting the generated image file to a server.

* * * * *